United States Patent
Keshipeddy

(10) Patent No.: US 12,049,223 B2
(45) Date of Patent: Jul. 30, 2024

(54) VEHICULAR DRIVING ASSIST SYSTEM RESPONSIVE TO DRIVER HEALTH MONITORING

(71) Applicant: Magna Electronics Inc., Auburn Hills, MI (US)

(72) Inventor: Prathyush Kumar Keshipeddy, Troy, MI (US)

(73) Assignee: Magna Electronics Inc., Auburn Hills, MI (US)

( * ) Notice: Subject to any disclaimer, the term of this patent is extended or adjusted under 35 U.S.C. 154(b) by 314 days.

(21) Appl. No.: 17/662,314

(22) Filed: May 6, 2022

(65) Prior Publication Data

US 2022/0363253 A1 Nov. 17, 2022

Related U.S. Application Data

(60) Provisional application No. 63/201,764, filed on May 12, 2021.

(51) Int. Cl.
| | |
|---|---|
| B60W 30/14 | (2006.01) |
| A61B 5/00 | (2006.01) |
| A61B 5/024 | (2006.01) |
| A61B 5/117 | (2016.01) |
| B60W 40/08 | (2012.01) |
| H04W 4/02 | (2018.01) |
| H04W 4/90 | (2018.01) |

(52) U.S. Cl.
CPC ....... *B60W 30/146* (2013.01); *A61B 5/02405* (2013.01); *A61B 5/117* (2013.01); *A61B 5/6831* (2013.01); *A61B 5/6893* (2013.01); *B60W 40/08* (2013.01); *H04W 4/025* (2013.01); *H04W 4/90* (2018.02); *B60W 2540/043* (2020.02); *B60W 2540/221* (2020.02); *B60W 2556/10* (2020.02); *B60W 2556/45* (2020.02)

(58) Field of Classification Search
CPC .............. B60W 30/146; B60W 40/08; B60W 2540/043; B60W 2540/221; B60W 2556/10; B60W 2556/45; A61B 5/02405; A61B 5/117; A61B 5/6831; A61B 5/6893; H04W 4/025; H04W 4/90; B60K 28/02; B60K 28/06
See application file for complete search history.

(56) References Cited

U.S. PATENT DOCUMENTS

| | | |
|---|---|---|
| 5,550,677 A | 8/1996 | Schofield et al. |
| 5,670,935 A | 9/1997 | Schofield et al. |
| 5,949,331 A | 9/1999 | Schofield et al. |

(Continued)

*Primary Examiner* — Yuen Wong
(74) *Attorney, Agent, or Firm* — HONIGMAN LLP

(57) ABSTRACT

A vehicular occupant health monitoring system includes a heartbeat sensor disposed at a vehicle and operable to capture sensor data measuring an aspect associated with the heart of an occupant of the vehicle. A control includes a processor operable to process sensor data captured by the heartbeat sensor and provided to the control. The vehicular occupant health monitoring system, responsive to processing by the processor of sensor data captured by the heartbeat sensor, determines whether the measured aspect associated with the heart of the occupant is abnormal. The vehicular occupant health monitoring system, responsive to determining the measured aspect associated with the heart of the occupant is abnormal, controls a function of the vehicle.

21 Claims, 3 Drawing Sheets

(56) References Cited

U.S. PATENT DOCUMENTS

| | | |
|---|---|---|
| 6,243,015 B1 | 6/2001 | Yeo |
| 6,485,081 B1 | 11/2002 | Bingle et al. |
| 6,621,411 B2 | 9/2003 | McCarthy et al. |
| 6,762,676 B2 | 7/2004 | Teowee et al. |
| 8,063,786 B2 | 11/2011 | Manotas, Jr. |
| 8,258,932 B2 | 9/2012 | Wahlstrom |
| 9,377,852 B1 | 6/2016 | Shapiro et al. |
| 9,750,420 B1 | 9/2017 | Agrawal et al. |
| 9,988,055 B1 | 6/2018 | O'Flaherty et al. |
| 11,433,906 B2 | 9/2022 | Lu |
| 11,618,454 B2 | 4/2023 | Lu |
| 2007/0055164 A1 | 3/2007 | Huang et al. |
| 2007/0257804 A1 | 11/2007 | Gunderson et al. |
| 2009/0156904 A1 | 6/2009 | Shen |
| 2009/0273487 A1 | 11/2009 | Ferro et al. |
| 2011/0018739 A1 | 1/2011 | Dehais |
| 2012/0150387 A1 | 6/2012 | Watson et al. |
| 2013/0070043 A1 | 3/2013 | Geva et al. |
| 2014/0152792 A1 | 6/2014 | Krueger |
| 2014/0167967 A1 | 6/2014 | He et al. |
| 2014/0306814 A1 | 10/2014 | Ricci |
| 2014/0336876 A1 | 11/2014 | Gieseke et al. |
| 2015/0009010 A1 | 1/2015 | Biemer |
| 2015/0015710 A1 | 1/2015 | Tiryaki |
| 2015/0022664 A1 | 1/2015 | Pflug et al. |
| 2015/0232030 A1 | 8/2015 | Bongwald |
| 2015/0258892 A1 | 9/2015 | Wu |
| 2015/0294169 A1 | 10/2015 | Zhou et al. |
| 2015/0296135 A1 | 10/2015 | Wacquant et al. |
| 2015/0352953 A1 | 12/2015 | Koravadi |
| 2016/0090097 A1 | 3/2016 | Grube et al. |
| 2016/0137126 A1 | 5/2016 | Fursich et al. |
| 2017/0105104 A1 | 4/2017 | Ulmansky et al. |
| 2017/0274906 A1 | 9/2017 | Hassan et al. |
| 2017/0311831 A1 | 11/2017 | Freer et al. |
| 2017/0337438 A1 | 11/2017 | el Kaliouby, Jr. et al. |
| 2017/0367590 A1 | 12/2017 | Sebe et al. |
| 2019/0110729 A1* | 4/2019 | Yamataka ............ A61B 5/1495 |
| 2020/0143560 A1 | 5/2020 | Lu et al. |
| 2020/0163560 A1 | 5/2020 | Chang et al. |
| 2020/0214614 A1 | 7/2020 | Rundo et al. |
| 2020/0283001 A1 | 9/2020 | Kulkarni |

\* cited by examiner

VEHICULAR DRIVING ASSIST SYSTEM RESPONSIVE TO DRIVER HEALTH MONITORING

CROSS REFERENCE TO RELATED APPLICATION

The present application claims the filing benefits of U.S. provisional application Ser. No. 63/201,764, filed May 12, 2021, which is hereby incorporated herein by reference in its entirety.

FIELD OF THE INVENTION

This disclosure relates generally to a vehicle driver monitoring system for a vehicle and, more particularly, to a vehicle driver monitoring system that utilizes one or more sensors at a vehicle.

BACKGROUND OF THE INVENTION

Monitoring a driver of a vehicle for inattention and fatigue using sensors is known.

SUMMARY OF THE INVENTION

Implementations herein provide a driving assistance system that includes A vehicular occupant health monitoring system, the vehicular occupant health monitoring system that includes a heartbeat sensor disposed at a vehicle equipped with the vehicular occupant health monitoring system. The heartbeat sensor is operable to capture sensor data measuring an aspect associated with the heart of an occupant of the vehicle. The system includes an electronic control unit (ECU) with electronic circuitry and associated software. The electronic circuitry includes a processor operable to process sensor data captured by the heartbeat sensor and provided to the ECU. The vehicular occupant health monitoring system identifies the occupant of the vehicle. The vehicular occupant health monitoring system, responsive to identifying the occupant, retrieves a profile associated with the occupant from a plurality of profiles stored in memory. The retrieved profile includes nominal health data of the occupant. The vehicular occupant health monitoring system, after retrieving the profile, and responsive to processing by the processor of sensor data captured by the heartbeat sensor, determines whether the measured aspect associated with the heart of the occupant is abnormal based on a comparison of the measured aspect with the nominal health data for that occupant. The vehicular occupant health monitoring system, responsive to determining the measured aspect associated with the heart of the occupant is abnormal, controls a function of the vehicle.

These and other objects, advantages, purposes and features of these implementations will become apparent upon review of the following specification in conjunction with the drawings.

DESCRIPTION OF THE PREFERRED EMBODIMENTS

A driver health monitoring system and/or driver assist system and/or advanced driver-assistance system and/or alert system operates to monitor a health or status of a driver using sensors that measure biological signals. The driver monitoring system includes a processor or processing system that is operable to receive sensor data from one or more sensors and provide an output to a system of the vehicle, a device of the driver, a remote server, a display device, etc.

Figure 1:
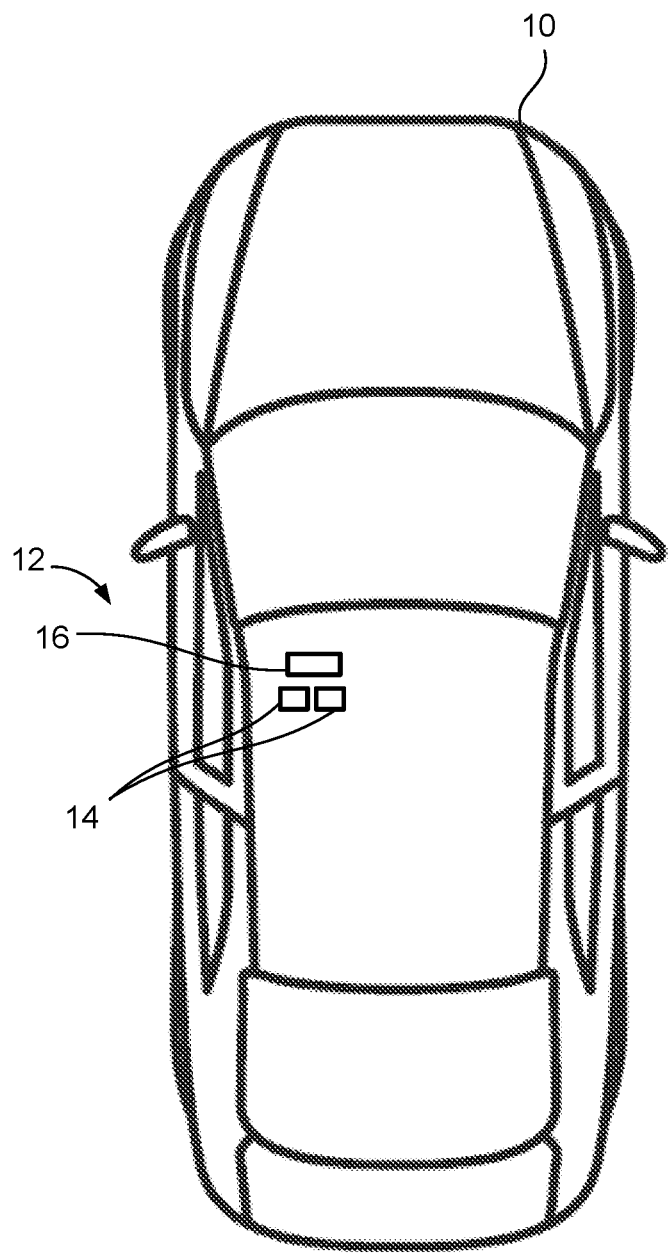
FIG. 1 is a plan view of a vehicle with a driver health monitoring system that incorporates sensors.

Referring now to the drawings and the illustrative embodiments depicted therein, a vehicle 10 includes a driver health monitoring system 12 that includes at least one sensor 14, such as a heartbeat sensor (FIG. 1). The sensor may include aspects of the driver monitoring system described in U.S. Publication No. US-2020-0283001, which is hereby incorporated herein by reference in its entirety. The driver health monitoring system 12 includes a control or electronic control unit (ECU) 16 having electronic circuitry and associated software, with the electronic circuitry including a data processor that is operable to process sensor data captured by the sensor or sensors. The ECU may process sensor data to detect a health or status or condition of the driver (e.g., driver fatigue or inattention). The data transfer or signal communication from the sensor 14 to the ECU may comprise any suitable data or communication link, such as wireless communication or a vehicle network bus or the like of the equipped vehicle.

Currently there is a lack of concrete solutions to determine the health status of the driver while driving or operating the vehicle. For example, when the health status of the driver is poor, the driver, other occupants in the vehicle, drivers/passengers in other vehicles, and pedestrians may all suffer harm from the poor health status (e.g., if the health status leads to erratic driving or an accident). Implementations herein include a driver health monitoring system that monitors a heartbeat of the driver to determine a health status of the driver and takes appropriate action based on the determined health status.

Figure 2:
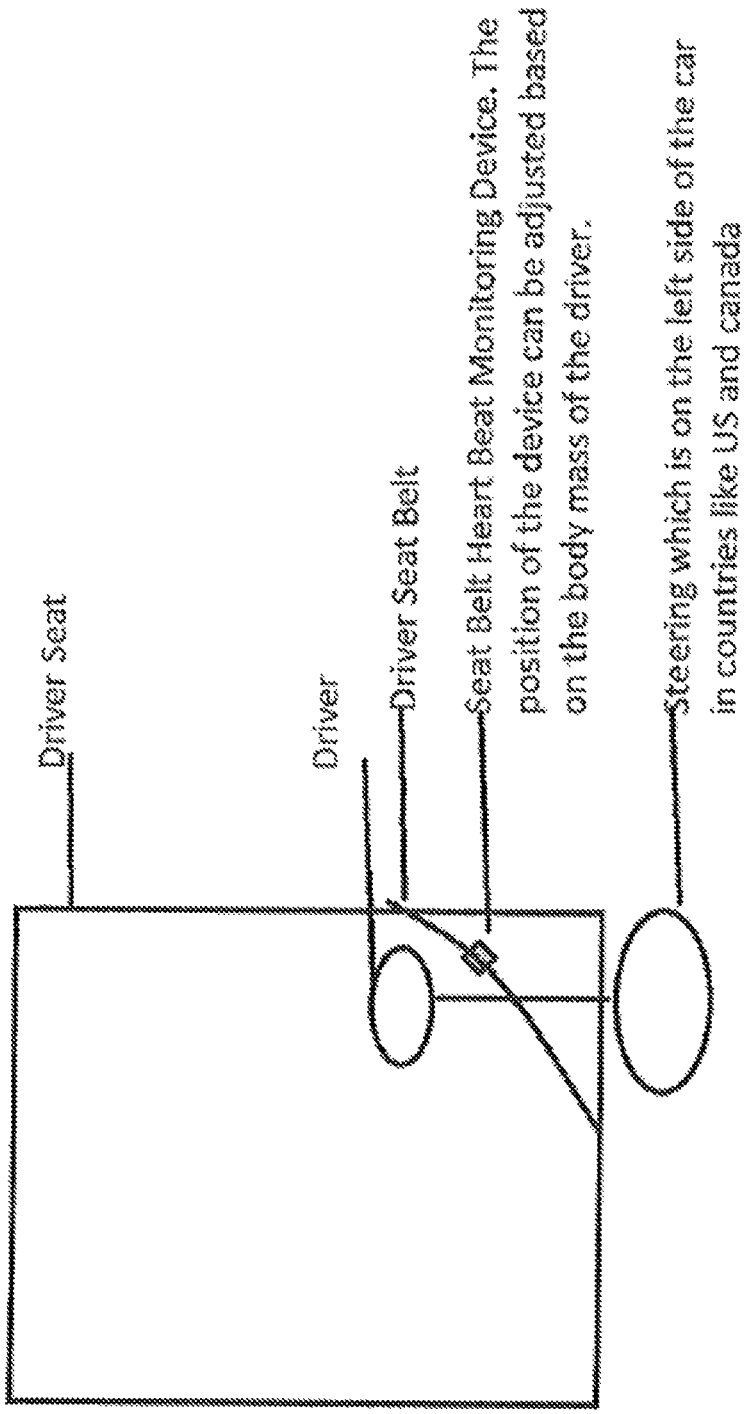
FIG. 2 is an interior cabin view of the driver health monitoring system of FIG. 1 in a right-hand traffic vehicle.

Referring now to FIG. 2, the system includes one or more heartbeat monitoring sensors or devices disposed at or within, for example, the seatbelt of the driver and/or the seatbelt of one or more passenger seats of the vehicle. Because the seatbelt stays close to the heart of the driver or other occupant, the sensor(s) may accurately and continuously monitor a heartrate and/or rhythm of the driver's heart. Based on monitoring the heartrate, rhythm, or other aspects of the heartbeat, the system may perform a number of different actions.

For example, when the system determines the heartrate of the driver is abnormal (e.g., too fast, too slow, irregular rhythm, etc.), the system may provide the driver or other occupants within the vehicle an alert. For example, the system may generate an alert on a display within the vehicle and/or provide an audible alert using speakers disposed within the vehicle and/or provide haptic feedback (e.g., vibrations of the seat or steering wheel). The system may provide other alerts as well. For example, the system may provide an alert to a mobile device of the driver or other user devices (e.g., other occupants or user devices permitted by the driver such as another family member or emergency contact). The system may provide an alert to medical professionals or emergency services. For example, when an extreme abnormality is detected (e.g., the driver's heart has appeared to stop), the system may automatically transmit an emergency message to emergency services (such as to the nearest emergency room or ambulance service or other service or location based on the current location of the vehicle). The system may provide a warning prior to transmitting the emergency message to provide an occupant of the vehicle the opportunity to halt transmission. The message may include the heartbeat data and/or location data (e.g., GPS data) indicating a current location of the vehicle.

As another example, the system may determine a normal or nominal heartrate and/or rhythm for a driver of a vehicle. For example, the system may monitor and record the driver's heartbeat during driving and store the values to determine a normal heartbeat/rhythm for that particular driver. The system may determine the identity of the particular driver via a driving profile (e.g., via the key used, a user input, an interior cabin camera using facial recognition, weight sensors, user devices such as mobile phones, etc.) and associate the heart data with the identity of the driver (i.e., with the profile of the driver). After determining and storing normal or nominal heart/health data, the system may determine, prior to the identified driver starting or operating the vehicle, the current heart data of the driver. As used herein, nominal heart data or nominal health data refers to any baseline, healthy, and/or target aspects of the heart (e.g., heart rate, blood pressure, rhythm, etc.) or any other health aspects that can be derived from heart data captured by the sensor. When the heart data of the driver appears abnormal (e.g., as compared to predetermined thresholds and/or the heart data stored for the identified driver with the profile of the driver), the system may alert the driver and/or prohibit the driver from starting or operating the vehicle. The alert or notification may indicate the details as to why the vehicle cannot be operated by the driver. The system may require detection of a heartbeat (or other signal) prior to allowing the vehicle to be operated. For example, with the heart sensor disposed at the driver's seatbelt, the system may prohibit a driver who does not wear his or her seatbelt from operating the vehicle.

The system may store any number of profiles (and associated nominal heart data) for any number of operators or potential operators and/or passengers of the vehicle. The profiles and associated data may be stored at the vehicle (e.g., on non-volatile memory disposed within the vehicle) or remote from the vehicle and retrieved via wireless communication (e.g., within a cloud database). For example, the system may communicate with a remote database via the Internet (using, for example, a cellular data network). The profile and data may be stored on a user device of the operator, and the vehicle may retrieve the data via a wireless connection with the user device (e.g., via BLUETOOTH). The system may periodically update the nominal health data stored with the profile using additional sensor data captured during subsequent trips in the vehicle.

When abnormal or irregular heartbeat data is detected while already operating the vehicle, the system may undertake a variety of actions. For example, the system may impose a speed limit on the vehicle (i.e., not allow the vehicle to surpass a predetermined speed). The system may force the vehicle to gradually stop and/or pull off the road. The system may engage hazard lights or other means of warning other vehicles. The system may interface with other driver assistance systems such as an adaptive cruise control (ACC) system. The system may provide speed limits or following distance limits to the ACC system when the system determines the driver's heartbeat data is abnormal.

Figure 3:
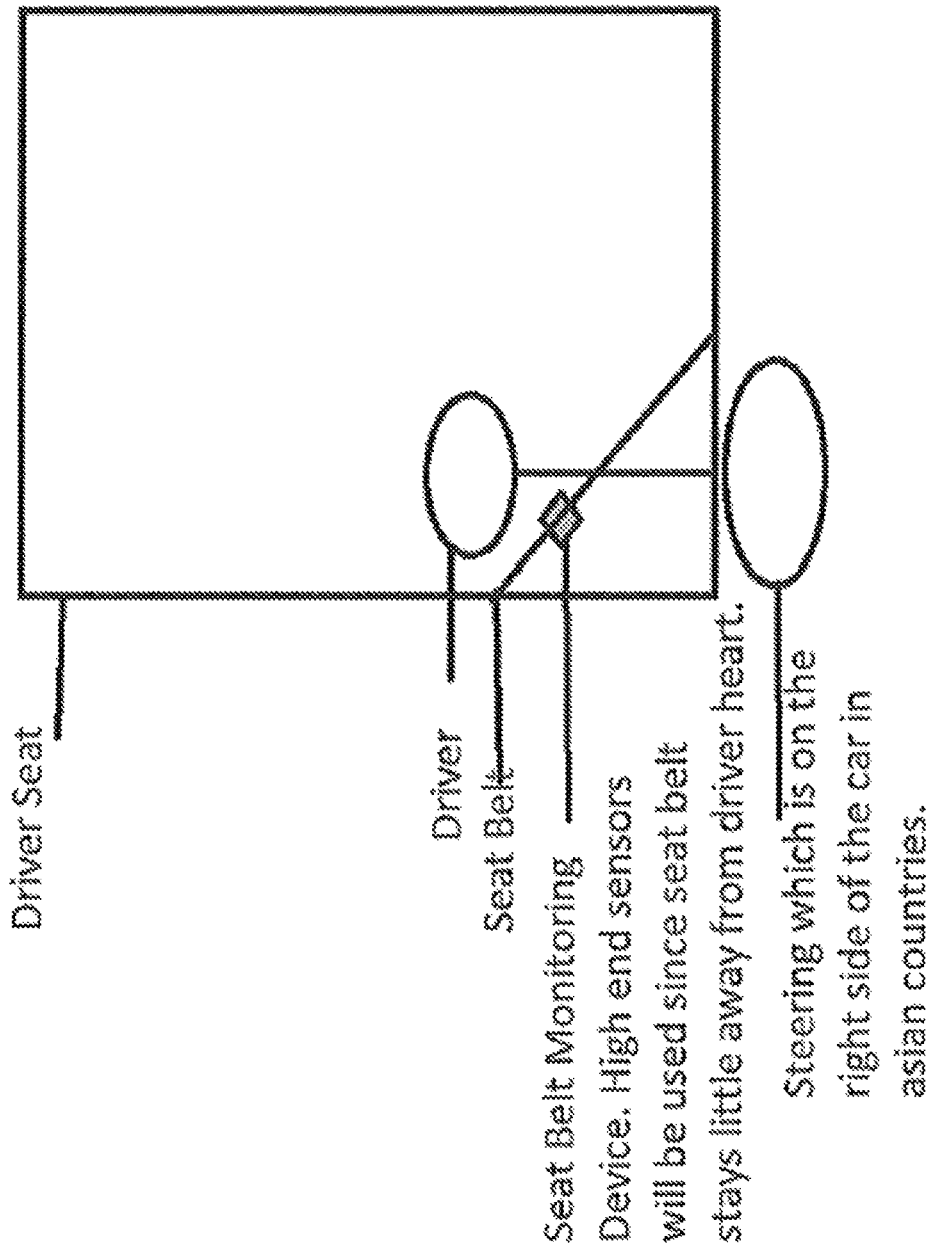
FIG. 3 is an interior cabin view of the driver health monitoring system of FIG. 1 in a left-hand traffic vehicle.

As shown in FIG. 2, the position of the sensor or device may be adjusted along the seatbelt based on the size of the driver. The system may be implemented in both right-hand traffic vehicles (FIG. 2) and left-hand traffic vehicles (FIG. 3).

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:

1. A vehicular occupant health monitoring system, the vehicular occupant health monitoring system comprising:
a heartbeat sensor disposed at a vehicle equipped with the vehicular occupant health monitoring system, wherein the heartbeat sensor is operable to capture sensor data measuring an aspect associated with a heart of an occupant of the vehicle;
an electronic control unit (ECU) comprising electronic circuitry and associated software, wherein the electronic circuitry comprises a processor operable to process the sensor data captured by the heartbeat sensor and provided to the ECU;
wherein the ECU identifies the occupant of the vehicle;
wherein the ECU, responsive to identifying the occupant, retrieves a profile associated with the identified occupant from a plurality of profiles stored in memory, and wherein the retrieved profile comprises nominal health data of the identified occupant;
wherein the ECU, after retrieving the profile, and responsive to processing by the processor of the sensor data captured by the heartbeat sensor, determines whether the measured aspect associated with the heart of the identified occupant is abnormal based on a comparison of the measured aspect with the nominal health data of the stored profile associated with the identified occupant;
wherein the ECU, after storing the nominal health data, updates the nominal health data based on additional sensor data captured by the heartbeat sensor; and
wherein the ECU, responsive to determining the measured aspect associated with the heart of the identified occupant is abnormal, controls a function of the vehicle, and wherein the function of the vehicle comprises speed of the vehicle, and wherein the ECU prohibits the speed of the vehicle from exceeding a predetermined threshold.

2. The vehicular occupant health monitoring system of claim 1, wherein the ECU determines whether the measured aspect associated with the heart of the identified occupant is abnormal by determining whether the measured aspect is different than the nominal health data by more than a threshold amount.

3. The vehicular occupant health monitoring system of claim 1, wherein the identified occupant is a driver of the vehicle, and wherein the ECU determines whether the measured aspect associated with the heart of the driver is abnormal prior to the identified driver operating the vehicle, and wherein, responsive to determining the measured aspect associated with the heart of the driver is abnormal, the ECU prohibits the driver from operating the vehicle.

4. The vehicular occupant health monitoring system of claim 1, wherein the function comprises an adaptive cruise control system.

5. The vehicular occupant health monitoring system of claim 4, wherein the ECU imposes a maximum speed limit on the adaptive cruise control system.

6. The vehicular occupant health monitoring system of claim 1, wherein the ECU, responsive to determining the measured aspect associated with the heart of the identified occupant is abnormal, transmits an alert to emergency services.

7. The vehicular occupant health monitoring system of claim 6, wherein the alert comprises (i) information associated with the measured aspect and (ii) a current location of the vehicle.

8. The vehicular occupant health monitoring system of claim 1, wherein the heartbeat sensor is disposed at a seatbelt of the vehicle.

9. The vehicular occupant health monitoring system of claim 8, wherein the heartbeat sensor is adjustable along a length of the seatbelt.

10. The vehicular occupant health monitoring system of claim 9, wherein the heartbeat sensor is adjustable to be located over the heart of the identified occupant when the identified occupant wears the seatbelt.

11. The vehicular occupant health monitoring system of claim 1, wherein the profile associated with the identified occupant stored in the memory of the vehicular occupant health monitoring system is based at least in part on the sensor data captured by the heartbeat sensor when the occupant first sat in the vehicle.

12. The vehicular occupant health monitoring system of claim 1, wherein the occupant is a driver of the vehicle.

13. A vehicular occupant health monitoring system, the vehicular occupant health monitoring system comprising:
a heartbeat sensor disposed at a seatbelt of a vehicle and operable to capture sensor data measuring an aspect associated with a heart of a driver of the vehicle;
an electronic control unit (ECU) comprising electronic circuitry and associated software, wherein the electronic circuitry comprises a processor operable to process the sensor data captured by the heartbeat sensor and provided to the ECU;
wherein the ECU identifies the driver of the vehicle seated in a driver seat of the vehicle;
wherein the ECU, responsive to identifying the driver, retrieves a profile associated with the identified driver from a plurality of profiles stored in memory of the vehicular occupant health monitoring system, and wherein the retrieved profile comprises nominal health data of the identified driver;
wherein the ECU, after retrieving the profile, and responsive to processing by the processor of the sensor data captured by the heartbeat sensor, determines whether the measured aspect associated with the heart of the identified driver is abnormal based on a comparison of the measured aspect with the nominal health data of the stored profile associated with the identified driver;
wherein the ECU, after storing the nominal health data, updates the nominal health data based on additional sensor data captured by the heartbeat sensor; and
wherein the ECU, responsive to determining the measured aspect associated with the heart of the identified driver is abnormal, controls a function of the vehicle, and wherein the function of the vehicle comprises speed of the vehicle, and wherein the ECU prohibits the speed of the vehicle from exceeding a predetermined threshold.

14. The vehicular occupant health monitoring system of claim 13, wherein the ECU determines whether the measured aspect associated with the heart of the identified driver is abnormal prior to the identified driver operating the vehicle, and wherein, responsive to determining the measured aspect associated with the heart of the identified driver is abnormal, the ECU prohibits the identified driver from operating the vehicle.

15. The vehicular occupant health monitoring system of claim 13, wherein the heartbeat sensor is adjustable along a length of the seatbelt.

16. The vehicular occupant health monitoring system of claim 15, wherein the heartbeat sensor is adjustable to be located over the heart of the identified driver when the identified driver wears the seatbelt.

17. A vehicular occupant health monitoring system, the vehicular occupant health monitoring system comprising:
a first heartbeat sensor disposed at a first seatbelt of a vehicle and operable to capture first sensor data measuring a first aspect associated with a heart of a driver of the vehicle;
a second heartbeat sensor disposed at a second seatbelt of the vehicle and operable to capture second sensor data measuring a second aspect associated with the heart of a passenger of the vehicle;
an electronic control unit (ECU) comprising electronic circuitry and associated software, wherein the electronic circuitry comprises a processor operable to process the first sensor data captured by the first heartbeat sensor and the second sensor data captured by the second heartbeat sensor and provided to the ECU;
wherein the ECU identifies the driver of the vehicle seated in a driver seat of the vehicle;
wherein the ECU identifies the passenger of the vehicle seated in a passenger seat of the vehicle;
wherein the ECU, responsive to identifying the driver, retrieves a first profile associated with the identified driver from a plurality of profiles stored in memory of the vehicular occupant health monitoring system, and wherein the retrieved first profile comprises first nominal health data of the first profile associated with the identified driver;
wherein the ECU, responsive to identifying the passenger, retrieves a second profile associated with the identified passenger from the plurality of profiles stored in memory of the vehicular occupant health monitoring system, and wherein the retrieved second profile comprises second nominal health data of the second profile associated with the identified passenger;
wherein the ECU, after retrieving the first profile, and responsive to processing by the processor of the first sensor data captured by the first heartbeat sensor, determines whether the measured first aspect associated with the heart of the identified driver is abnormal based on a comparison of the measured first aspect with the first nominal health data;
wherein the ECU, after storing the nominal health data of the first profile, updates the nominal health data of the first profile based on additional first sensor data captured by the first heartbeat sensor;
wherein the ECU, after retrieving the second profile, and responsive to processing by the processor of the second sensor data captured by the second heartbeat sensor, determines whether the measured second aspect associated with the heart of the identified passenger is abnormal based on a comparison of the measured second aspect with the second nominal health data;
wherein the ECU, after storing the nominal health data of the second profile, updates the nominal health data of the second profile based on additional second sensor data captured by the second heartbeat sensor; and wherein the ECU controls a function of the vehicle responsive to at least one selected from the group consisting of (i) determining the measured first aspect associated with the heart of the identified driver is abnormal and (ii) determining the measured second aspect associated with the heart of the identified passenger is abnormal, and wherein the function of the vehicle comprises speed of the vehicle, and wherein the ECU prohibits the speed of the vehicle from exceeding a predetermined threshold.

18. The vehicular occupant health monitoring system of claim 17, wherein the function comprises an adaptive cruise control system.

19. The vehicular occupant health monitoring system of claim 17, wherein the function includes an alert system.

20. The vehicular occupant health monitoring system of claim 19, wherein the alert system transmits an alert to emergency services.

21. The vehicular occupant health monitoring system of claim 20, wherein the alert comprises (i) information associated with the measured first aspect or with the measured second aspect and (ii) a current location of the vehicle.

\* \* \* \* \*